United States Patent [19]

Ishikawa et al.

[11] 4,219,730
[45] Aug. 26, 1980

[54] CHARGE-PARTICLE ENERGY ANALYZER

[75] Inventors: Isao Ishikawa, Hino; Yoshitaka Goto, Sayama; Michiyasu Itoh, Iruma, all of Japan

[73] Assignee: Hitachi, Ltd., Japan

[21] Appl. No.: 936,928

[22] Filed: Aug. 25, 1978

[30] Foreign Application Priority Data

Aug. 29, 1977 [JP] Japan .................................. 52-102706

[51] Int. Cl.$^2$ ...................... H01J 39/00; G01M 23/00
[52] U.S. Cl. ..................................... 250/305; 250/310
[58] Field of Search ............................ 250/305, 310

[56] References Cited
U.S. PATENT DOCUMENTS

| | | | |
|---|---|---|---|
| 3,596,091 | 7/1970 | Helmer et al. .................. | 250/305 |
| 3,714,417 | 1/1973 | Anderson ........................ | 250/305 |
| 4,126,782 | 11/1978 | Usami et al. .................... | 250/305 |

*Primary Examiner*—Harold A. Dixon
*Attorney, Agent, or Firm*—Craig and Antonelli

[57] ABSTRACT

A charged-particle energy analyzer having means for irradiating a sample with a primary electron beam, deflecting electrode means which focus charged particle flux emitted from the sample onto a center axis of the primary electron beam or onto an identical circumference with its center on the axis, a slit disposed at the focus point of the charged particles, an energy analyzer whose object point lies at the focus point, a detector for detecting the charged particles analyzed by the energy analyzer, and charged particle flux deflecting means provided between the sample and the detector, for shielding by one part of the charged particle flux focused in a true circular form, to thereby make it possible not only to set a wide accepted solid angle for signals but also to get an information as to the concave or convex surface condition of the sample at the measured portion.

4 Claims, 4 Drawing Figures

CHARGE-PARTICLE ENERGY ANALYZER

BACKGROUND OF THE INVENTION

This invention relates to a charged-particle energy analyzer. More particularly, it relates to a charged-particle energy analyzer for use in the surface analysis of a solid based on electron beams such as Auger electrons.

In analyzing a feeble electron beam of low energy such as Auger electrons and photoelectrons in the surface analysis of a solid, it is important to efficiently utilize the electrons emitted from the sample. To this end, the accepted solid angle (the solid angle of an electron beam entering an analyzer/the solid angle of an electron beam emitted from a sample) needs to be great.

As the optimum configuration for such a requirement, an analyzing system of a structure shown in FIG. 1 has already been proposed (Official Gazette of Japanese Open-laid Patent Application No. 96091/1977). This apparatus has a construction wherein a deflecting system consisting of two, inner and outer electrodes is arranged axially symmetrically around a sample, so that charged particles emitted from the sample and entering into the deflecting system draw a sharply curved track, whereupon they focus onto a center axis or onto a circumference with its center on the axis again. Behind the deflecting system, an analyzer is arranged at a position having such an electrooptical relation that the focus point is considered as the emission point of a signal. Thus, the detection of secondary electrons or the energy analysis of photoelectrons, Auger electrons etc. is effected.

Referring to FIG. 1, numeral 1 designates an electron gun. An electron beam 2 generated therefrom is focused by a focusing lens 3, and is focused on a sample 4. Charged particles 5 such as secondary electrons and Auger electrons are emitted from the irradiated point of the sample 4 in a spacial distribution conforming substantially with the cosine law. Among the charged particles, an electron flux surrounded between two cones whose vertices lie at point P and which have half vertical angles of $\theta+$ a and $\theta-$ a respectively enter the interspace between deflecting electrodes 6 and 7. The deflecting electrodes 6 and 7 constitute a double electrode system which is axially symmetric and which has an L-shaped section.

The charged particle flux is advanced along a sharply curved track by a deflecting electric field in the deflecting electrode system. Further, it has the track corrected by an auxiliary electrode 8 and converges on a slit 9 posterior to the auxiliary electrode 8 in the first order of the very small angle a. After passing through the slit 9, it advances so as to cross on a center axis. The charged particle flux is subjected to an energy analysis by a cylindrical mirror type analyzer 10 arranged in the next stage, and only the charged particles having certain specified energy converge on a detecting slit 9' located on the axis. A signal is detected by a detector 11 which is disposed behind the detecting slit 9'.

Voltages which are applied to the respective electrodes of the deflecting electrodes 6 and 7, the auxiliary electrode 8 and the cylindrical mirror type analyzer 10 are appropriately selected with power sources 12, 13 and 14, and the applied voltage values are thereafter scanned at a fixed ratio. Then, in case of e. g. the Auger electron analysis, the electron energy spectrum emitted from the sample can be obtained because the electron track depends upon the energy.

In the above, the analysis of Auger electrons emitted from the sample has been described as an example. In this case, a switch $S_1$ located at a stage succeeding to the detector 11 is kept thrown onto an A side. The detected signal is amplified by a lock-in amplifier 15, and is subjected to a sensitive phase detection by the use of a perturbation A. C. at a frequency f. When the amplified signal is recorded by a recorder 16, the Auger electron energy spectrum can be obtained here.

On the other hand, the power sources 12, 13 and 14 are fixed at predetermined voltage values so as to detect only Auger electrons having specified energy. Under this state, the switch $S_1$ is kept thrown onto a B side, a deflecting coil 19 of a cathode-ray tube 20 and a deflecting coil 18 for the primary electron beam are synchronously driven by a power source 17, the primary electron beam is scanned on the sample, and the intensity of the signal which is produced in correspondence with the scanned position of the sample surface and which responds to the Auger electrons of the specified energy value is used for the brightness modulation of the CRT 20. Then, an Auger electron scanning image of a specified element corresponding to the scanning area of the primary electron beam can be displayed on the screen of the CRT 20.

The foregoing description has been made of the operating procedures of the ultrahigh sensitivity Auger electron analyzer which has heretofore been used. With the prior-art method, the signal charges emitted from the sample are detected from all directions, and hence, it is difficult to discriminate whether the intensity of the detected signal is truly founded on the quantity of the element contained in the sample or it is related with the shape (concave or convex condition) of the sample surface in the measured place.

SUMMARY OF THE INVENTION

This invention has been made in view of the above-mentioned drawback, and has for its object to provide a charged-particle energy analyzer which makes it possible to set a wide accepted solid angle for signals and also to get a discriminative information on the concave or convex condition of a sample surface at a measured position.

In order to accomplish the object, according to this invention, electrical means for deflecting the charged particle flux is disposed between the deflecting electrode means and the slit in the construction shown in FIG. 1 so as to deflect part of the charged particle flux focused in a true circular form and to prevent it from entering the slit.

BRIEF DESCRIPTION OF THE DRAWINGS

FIG. 3A is a partial view showing the details of electon flux deflecting means in this invention, while

DETAILED DESCRIPTION OF THE PREFERRED EMBODIMENT

Hereunder, this invention will be described in detail in connection with an embodiment.

Figure 2:
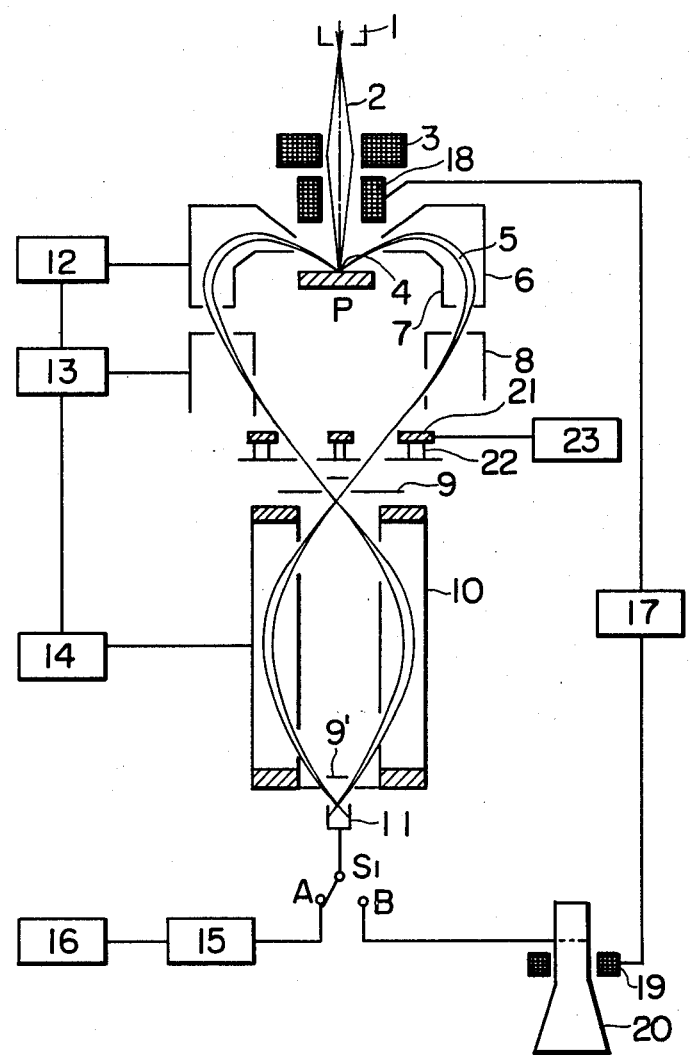
FIG. 2 is a view showing an embodiment of a charged-particle energy analyzer according to this invention.
Figure 3A:
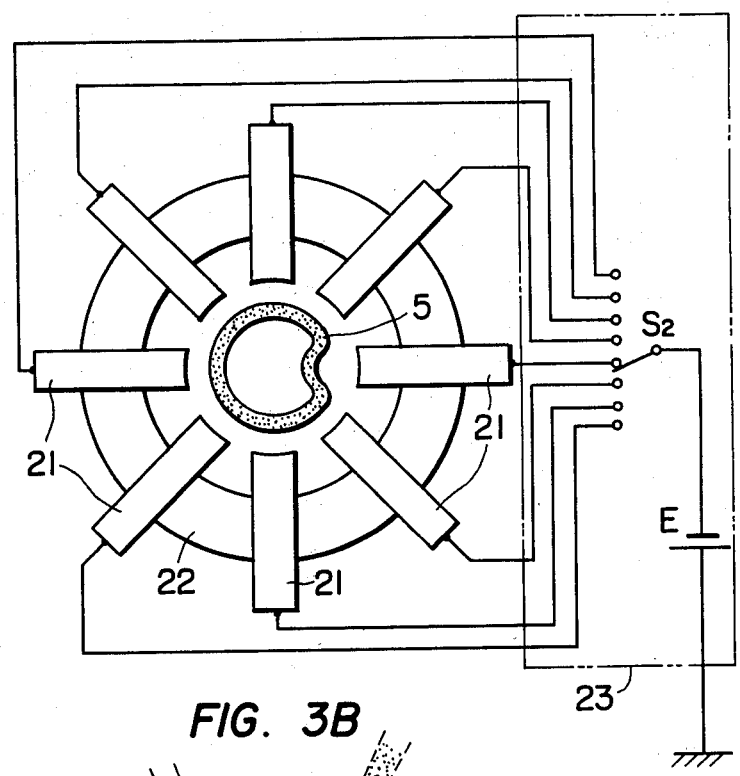
Figure 3B:
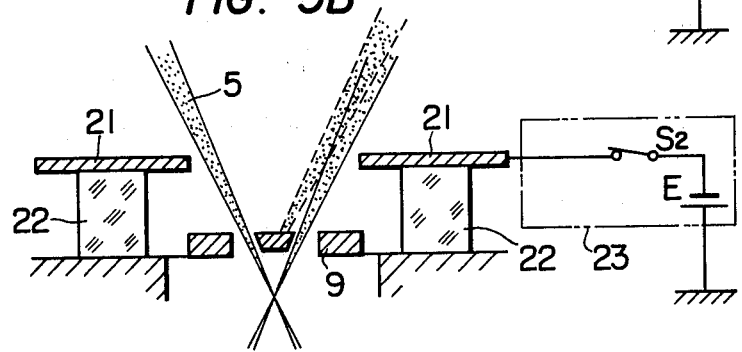
FIG. 3B is a schematic sectional view of a part of the means.

FIG. 2 shows an embodiment of an electrostatic type charged particle energy analyzing system which is equipped with the charged particle flux deflecting means stated previously. FIG. 3A is a plan view showing the details of the charged particle deflecting means, while FIG. 3B is a schematic vertical sectional view of a part of the means.

Various portions will now be explained.

Figure 1:
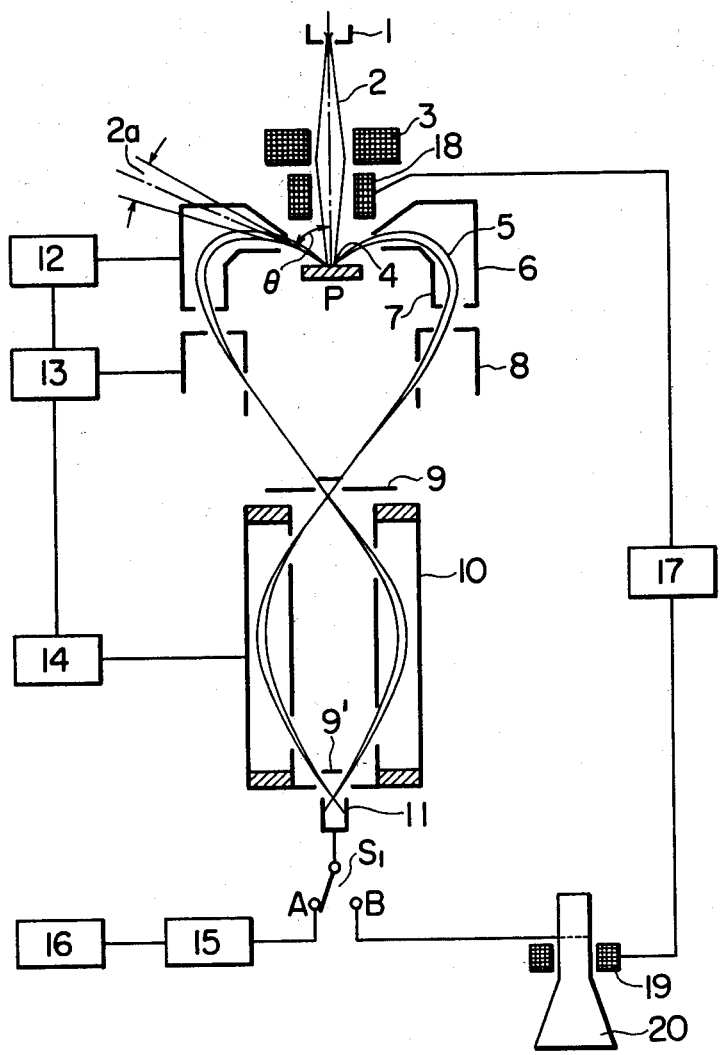
FIG. 1 is a view showing a charged-particle energy analyzer in a prior art.

Referring to FIG. 2, the structure of the charged particle flux deflecting means is such that charged particle flux deflecting electrodes 21 are fixed above the slit 9 through an insulator 22. The plurality of deflecting electrodes are arranged axially symmetrically. Here, the fore ends or inner ends of the deflecting electrodes are located so that the charged particle flux to enter the slit may not be intercepted. The voltage application to the deflecting electrodes 21 can be effected with a power source 23. Numerals 1 to 20 cited in FIG. 2 designate the same parts as in FIG. 1.

In the analyzing system thus constructed, first of all, the voltages to be applied to the analyzing system are set by the power sources 12, 13 and 14 at values at which charged particles to be emitted from the sample can be detected most efficiently. Under this state, the sample surface is scanned by the primary electron beam with the scanning power source 17, and signals detected on the basis of the charged particles emitted from the sample are displayed on the CRT 20. Then, the secondary electron image of the sample surface can be obtained thereon. In this case, the charged particle flux to enter the charged particle flux deflecting means is corrected and adjusted in advance so as to form a true circular ring.

Subsequently, a voltage is applied to one of the deflecting electrodes in specified direction so as to deflect part of the charged particle flux 5 and to prevent it from passing through the slit 9. A secondary electron image obtained as a result is equivalent to one which is obtained when the sample is irradiated by the primary electron beam in a certain specified direction. In case where a concave or convex part exists on the sample surface, it can be observed in three dimensions.

As illustrated in FIGS. 3A and 3B, the voltage capable of deflecting the charged particle flux to a position at which the flux cannot pass through the slit can be applied to the deflecting electrode 21. Part of the signal in every direction is sequentially deflected by sequentially changing-over switches $S_2$, and the sample surface is observed each time. Thus, what shape the concave or convex part of the sample surface has can be discerned. By observing the element distribution image based on the Auger electron analysis with this information borne in mind, it becomes possible to interpret the image with the influence of the shape effect of the sample scrupulously taken into account.

In the above, description has been made of the embodiment wherein the charged particle flux deflecting means 21 is arranged between the deflecting electrode 8 and the slit 9. In this invention, however, the charged particle flux deflecting means may be installed in any place between the sample being a signal generating source and the deflecting system, the analyzing system or the detector. If the single means is insufficient, the object can be achieved by disposing a plurality of deflecting means at any desired positions in the track of the signal.

In the above embodiment of this invention, it has been described that the signal of part of the charged particle flux 5 is made undetectable by electrostatically deflecting the part with the deflector plates. Needless to say, however, the same effect can be expected for the interception of part of the charged particle flux in such a way that a plurality of shield plates are arranged axially symmetrically, one or more of the shield plates being movable to positions at which they can intercept the charged particle flux, and that the shield plates corresponding to respective directions are moved to intercept the charged particle flux.

We claim:

1. A charged-particle energy analyzer comprising means for irradiating a sample with a primary charged particle beam, said sample being mounted in a perpendicular direction to a center axis of said primary charged particle beam, deflecting electrode means for focusing a a charged particle flux emitted from the sample onto the center axis of said primary charged particle beam or onto an identical circumference with its center on the axis, slit means disposed at a focus position of the charged particle flux, energy analysis means with its object point lying at the focus position and arranged for analyzing energy of the charged particles, detection means for detecting said charged particles analyzed by said energy analysis means, and charged particle flux deflecting disposed in the peripheral vicinity of a path of said charged particle flux between said sample and said detection means, said charged particle flux deflecting means enabling interception of part of the charged particle flux entering thereinto in an angular range of all directions within a plane perpendicular to the axis, said charged particle flux deflecting means comprising a plurality of shield plates which are arranged axially symmetrically in the vicinity of a path of said charged particle flux between said sample and said detection means, said each shield plate being movable to a position at which it intercepts part of said charged particle flux.

2. A charged-particle energy analyzer comprising means for irradiating a sample with a primary charged particle beam, said sample being mounted in a perpendicular direction to a center axis of said primary charged particle beam deflecting electrode means for focusing a charged particle flux emitted from the sample onto the center axis of said primary charged particle beam or onto an identical circumference with its center on the axis, slit means disposed at a focus position of the charged particle flux energy analysis means with its object point lying at the focus position and arranged for analyzing energy of the charged particles, detection means for detecting said charged particles analyzed by said energy analysis means, and charged particle flux deflecting means disposed in the peripheral vicinity of a path of said charged particle flux between said sample and said detection means, said charged particle flux deflecting means enabling interception of part of the charged particle flux entering thereinto in an angular range of all directions within a plane perpendicular to the axis, said charged particle flux deflecting means comprising a plurality of shield plates which are arranged axially symmetrically in the vicinity of a path of said charged particle flux between said deflecting electrode means and said slit means, said each shield plate being movable to a position at which it intercepts part of said charged particle flux that is focused in a true circular form.

3. A charged-particle energy analyzer according to claim 4 or claim 2, wherein said energy analysis means is a cylindrical mirror type energy analyzer.

4. A charged-particle energy analyzer according to claim 1 or claim 2, wherein said charged particle flux deflecting means includes eight of said shield plates.

* * * * *